United States Patent
Sanchez-Zambrano

(10) Patent No.: US 6,279,677 B1
(45) Date of Patent: Aug. 28, 2001

(54) DISPOSABLE DIAPHRAGM STETHOSCOPE

(76) Inventor: Sergio Sanchez-Zambrano, Rte. 5, Box 35A, Clebume, TX (US) 76031

( * ) Notice: Subject to any disclaimer, the term of this patent is extended or adjusted under 35 U.S.C. 154(b) by 0 days.

(21) Appl. No.: 09/526,325

(22) Filed: Mar. 15, 2000

Related U.S. Application Data

(60) Provisional application No. 60/124,688, filed on Mar. 16, 1999.

(51) Int. Cl.$^7$ .......................................................... A61B 7/02
(52) U.S. Cl. ............................................. 181/131; 181/137
(58) Field of Search .................................... 181/131, 137; 381/67

(56) References Cited

U.S. PATENT DOCUMENTS

| | | |
|---|---|---|
| 1,845,795 * | 2/1932 | Joseph ................................... 181/131 |
| 3,276,536 | 10/1966 | Littmann . |
| 3,614,991 * | 10/1971 | Matchlup et al. ................... 181/131 |
| 3,867,925 | 2/1975 | Ersek . |
| 4,475,619 | 10/1984 | Packard . |
| 4,867,268 | 9/1989 | Ulert . |
| 5,420,382 * | 5/1995 | Katz ..................................... 181/131 |
| 5,424,495 | 6/1995 | Wurzburger . |
| 5,448,025 | 9/1995 | Stark et al. . |
| 5,466,897 | 11/1995 | Ross et al. . |
| 6,019,186 | 2/2000 | Zambrano . |

* cited by examiner

Primary Examiner—Khanh Dang
(74) Attorney, Agent, or Firm—Bracewell & Patterson, L.L.P.

(57) ABSTRACT

A stethoscope head for joining to an earpiece assembly. The head has a generally tubular neck for joining the head to the earpiece assembly. An anterior chamber has an open face with an aperture at its apex and an outer rim. The bell is adapted to gather and reflect sound originating at or near the open face toward the aperture. A thin disposable diaphragm has adhesive on one side for releasably adhering to the rim. A central chamber is adjacent the bell and connected to the bell by the aperture. The chamber is adapted to direct sounds from the aperture to the neck.

18 Claims, 2 Drawing Sheets

DISPOSABLE DIAPHRAGM STETHOSCOPE

This application claims the benefit of provisional patent application Ser. No. 60/124,688, filed Mar. 16, 1999.

TECHNICAL FIELD OF THE INVENTION

The present invention relates in general to medical devices, and more particularly to a stethoscope with a disposable diaphragm to reduce transmission of pathogens and acoustic chambers to enhance cardiac and pulmonary sounds.

BACKGROUND OF THE INVENTION

Stethoscopes are used by medical practitioners to listen to the sounds emitted by internal organs of patients. It is common for some medical practitioners to use the same stethoscope on every patient without thoroughly cleaning the stethoscope after each use. Transmission of infection through contaminated medical devices is well documented, and stethoscopes have recently been shown to harbor various organisms on their diaphragm surface. The practice of using the same stethoscope on multiple patients without thoroughly cleaning the stethoscope increases the risk of spreading germs and bacteria from one patient to another.

There are a number of devices shown in the prior art to prevent spreading of germs with stethoscopes. These devices generally comprise disposable covers which are releasably secured over the diaphragm. However, because theses covers are designed to be used with existing stethoscopes, the stethoscope is still functional without the cover and is likely to be used without the covering. Other devices comprise several components with moving parts, such as a covering that screws on over the bell. The moving parts increase the cost and complexity of the stethoscope.

Therefore, there is a need for a stethoscope with no moving parts that encourages use of the disposable diaphragm. Additionally, the stethoscope should have strong acoustic capabilities expected of a stethoscope as a diagnostic tool.

SUMMARY OF THE INVENTION

The present invention is drawn to a stethoscope head for joining to an earpiece assembly. The head has a generally tubular neck for joining the head to the earpiece assembly. An anterior acoustic chamber and a posterior chamber are connected by a body having an open face with a central passage. The body has an outer rim surrounding the anterior acoustic chamber. A thin, disposable diaphragm has adhesive on one side for releasably adhering to the rim thereby covering the anterior acoustic chamber. An acoustic tunnel extends from the posterior acoustic chamber thought the neck for delivering sound waves to the earpiece assembly. The anterior acoustic chamber has reflective walls oriented to direct sound waves passing through the central passage into the tunnel.

The anterior acoustic chamber is generally bowl shaped and the central passage is located at an axis of the anterior acoustic chamber. The rim is flat. The central passage has a transverse cross-sectional area smaller than a cross-sectional area of the posterior acoustic chamber taken along a plane parallel to the first mentioned cross-sectional area. The tunnel is substantially at a right angle along a straight line to an axis of the anterior acoustic chamber. The posterior acoustic chamber has a first reflecting wall portion and a second wall portion. The first wall portion is located on an axis of the anterior acoustic chamber and oriented to reflect sound waves to the second wall portion which in turn is oriented to reflect sound waves into the tunnel. The second wall portion is spaced farther from the tunnel than the first wall portion. The anterior acoustic chamber is free of any structure between the central passage and the diaphragm.

DETAILED DESCRIPTION OF THE INVENTION

Figure 1:
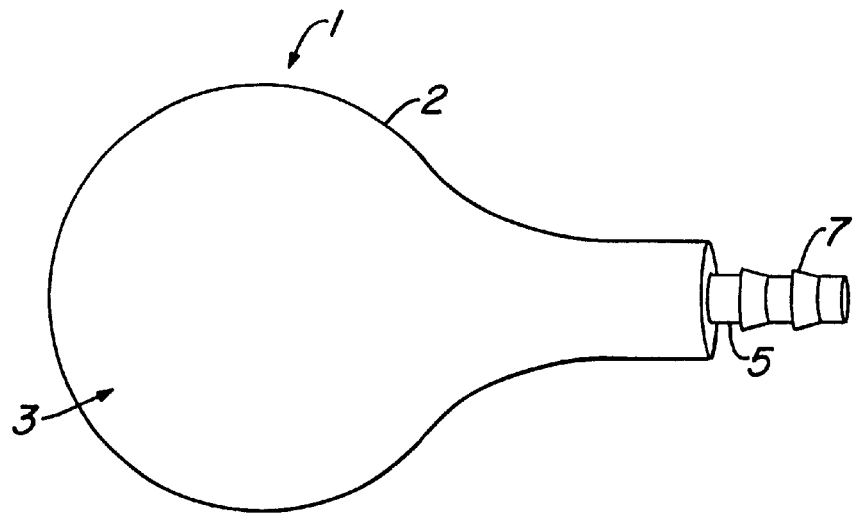
FIG. 1 is an elevated view of the bottom side of the improved stethoscope.

Referring now to FIG. 1, an elevated view of the improved stethoscope 1 is shown. Improved stethoscope 1 has head 2 having a bottom side 3. Neck 5 extends outwardly from head 2 and terminates for connection to an ear-piece assembly, not shown. Neck 5 has a ribbed external surface 7 to tightly engage tubes that are generally integral with the ear-piece assembly. Neck 5 is tubular in shape and defines a sound conducting tunnel 9 (FIG. 3) therethrough for transmitting auscultatory sounds collected by head 2 to the ear-piece assembly. The ribbed external surface 7 of neck 5 is adaptable for connection with any ear-piece assembly currently available in the art. Preferably, improved stethoscope 1 is made out of a hard, durable, plastic and graphite mixture that provides for transmission of the auscultatory sounds and extends the operational use of improved stethoscope 1.

Figure 2:
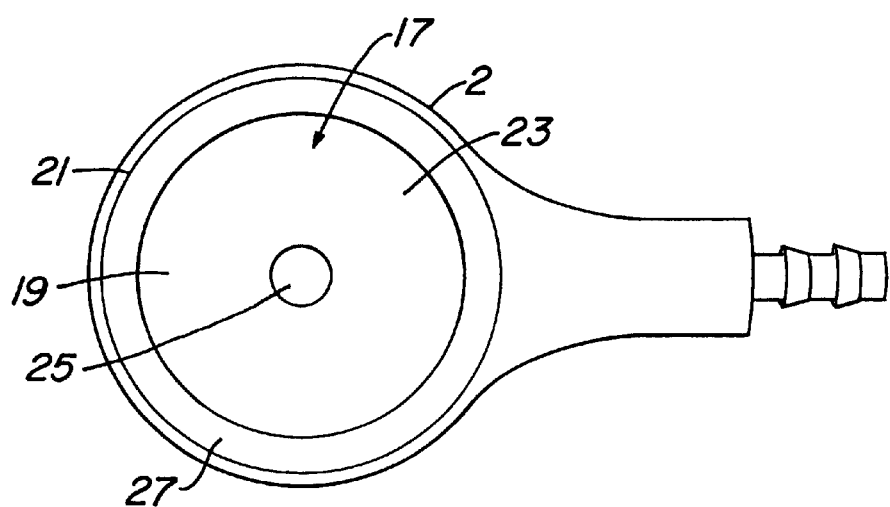
FIG. 2 is an elevated view of the top side of the improved stethoscope without the disposable diaphragm.
Figure 3:
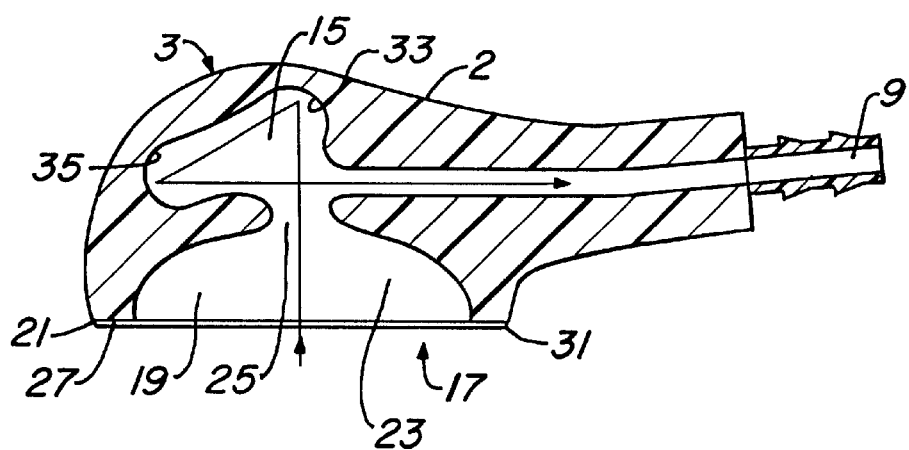
FIG. 3 is a side view of the improved stethoscope.

Referring now to FIG. 2, an elevated view of the top side 17 of improved stethoscope 1 is shown. Head 2 is generally circular in shape and has an open face 19 for receiving acoustical input. Open face 19 is defined at its perimeter by rim 21 that travels the circumference of head 2. A bell shaped anterior chamber 23 recedes radially inward from rim 21 and terminates at a central sound conducting passage 25. Central passage 25 is on the central axis of anterior chamber 23 and tunnel 9 is substantially at a right angle along a straight line to the central axis of anterior chamber 23 (FIG. 3). Rim 21 has flat surface 27 for engagement with a disposable diaphragm 31 (FIG. 3).

The shape of anterior chamber 23 from rim 21 to passage 25 is such that auscultatory sounds originating at or near the surface of anterior chamber 23 are reflected towards passage 25. Head 2 is in acoustical communication with neck 5 such that auscultatory sounds gathered at or near surface of anterior chamber 23 travel along an acoustic path from anterior chamber 23 through passage 25, through neck 5, and ultimately to the ear piece.

FIG. 3 shows a cross-sectional view of the improved stethoscope 1. Disposable diaphragm 31 is a flat, thin disk attached by non-aggressive adhesion to surface 27 of rim 21. Anterior chamber 23 terminates and forms sound conducting passage 25. In posterior chamber 15 sounds received through passage 25 are reflected through sound conducting tunnel 9 formed by neck 5, and ultimately to the ear-piece assembly. The transverse cross-sectional area of passage 25 is smaller than the cross-sectional area of the posterior chamber 15 when measured at a parallel plane.

FIG. 3 also shows the acoustical path of sound originating at or near open face 19 of head 2. Auscultatory sound is collected by contact with disposable diaphragm 31 or with rim surface 27. Disposable diaphragm 31 vibrates when in contact with auscultatory sound waves. The radial inward recession and rounded contour of anterior chamber 23 focuses the auscultatory sounds to sound conducting passage 25. Sound travels through passage 25 and reflects off of a first wall 33 in posterior chamber. First wall 33 is generally aligned with the central axis of anterior chamber 23 and positioned to reflect the sound to a second wall 35, which in turn is oriented to reflect sound waves into tunnel 9. Second wall 35 is spaced farther from the tunnel than first wall 33.

After each use, the disposable diaphragm 31 may be detached from rim surface 27 and discarded. A new disposable diaphragm 31 may then be re-adhered to rim surface 27.

The invention has several advantages. As stethoscope diaphragms have been shown to harbor potentially pathogenic bacteria, one advantage is that the use of a disposable diaphragm prevents cross-contamination among patients. Another advantage is that the invention functions only with disposable diaphragms, and thus forces the user of the invention to minimize contamination by interchanging the disposable diaphragm after each use. Another advantage of the present invention is the improved acoustical properties of the anterior chamber and posterior chamber. Further advantages include the lack of mobile parts on the invention, the adaptability of the improved stethoscope to any and all ear-piece assemblies currently available in the market, and the use of a hard, durable plastic and graphite mixture that provides for acoustic transmission and extended duration of the piece.

While the invention has been shown in only one of its forms, it should be apparent to those skilled in the art that it is not so limited, but is susceptible to various changes without departing from the scope of the invention.

I claim:

1. A stethoscope head for joining to an earpiece assembly, comprising:
   a generally tubular neck for joining the head to the earpiece assembly;
   an anterior acoustic chamber and a posterior acoustic chamber connected by a body having an open face with a central passage, the body having an outer rim surrounding the anterior acoustic chamber;
   a thin, disposable diaphragm having adhesive on one side for releasably adhering to the rim thereby covering the anterior acoustic chamber;
   an acoustic tunnel extending from the posterior acoustic chamber through the neck for delivering sound waves to the earpiece assembly; and
   wherein the anterior acoustic chamber has reflective walls oriented to direct sound waves passing through the central passage into the tunnel.

2. The stethoscope head of claim 1 further comprising a plurality of indentations in an exterior surface of the body opposite the rim for gripping by a user.

3. The stethoscope head of claim 1 wherein the rim is flat.

4. The stethoscope head of claim 1 wherein the anterior acoustic chamber is generally bowl shaped and wherein the central passage is located at an axis of the anterior acoustic chamber.

5. The stethoscope head of claim 1 wherein the central passage has a transverse cross-sectional area smaller than a cross-sectional area of the posterior acoustic chamber taken along a plane parallel to said first mentioned cross-sectional area.

6. The stethoscope head of claim 1 wherein the tunnel is substantially at a right angle along a straight line to an axis of the anterior acoustic chamber.

7. The stethoscope head of claim 1 wherein the posterior acoustic chamber has a first reflecting wall portion and a second wall portion, the first wall portion located on an axis of the anterior acoustic chamber and oriented to reflect sound waves to the second wall portion which in turn is oriented to reflect sound waves into the tunnel.

8. The stethoscope head of claim 7 wherein the second wall portion is spaced farther from the tunnel than the first wall portion.

9. The stethoscope head of claim 1 wherein the anterior acoustic chamber is free of any structure between the central passage and the diaphragm.

10. A stethoscope comprising:
    a bowl shaped chamber with an open end and a rim about the circumference of the open end;
    a secondary chamber adjacent to the bowl shaped chamber and in acoustic communication with the bowl shaped chamber by a central passage;
    an acoustic tunnel extending outward from the secondary chamber, substantially at a right angle along a straight line to an axis of the bowl shaped chamber;
    wherein the secondary chamber has a first reflecting wall portion and a second reflecting wall portion, the first reflecting wall portion is located on an axis of the bowl shaped acoustic chamber oriented to reflect sound waves to the second wall portion which in turn is oriented to reflect sound waves into the tunnel.

11. The stethoscope of claim 1 further comprising a plurality of indentations in an exterior surface of the body opposite the rim for gripping by a user.

12. The stethoscope of claim 1 wherein the rim is flat.

13. The stethoscope of claim 1 wherein the central passage has a transverse cross-sectional area smaller than a cross-sectional area of the secondary chamber taken along a plane parallel to the first mentioned cross-sectional area.

14. The stethoscope of claim 1 wherein the second wall portion is spaced farther from the tunnel than the first wall portion.

15. The stethoscope of claim 1 wherein the bell shaped chamber is free of any structure between the central passage and the diaphragm.

16. The stethoscope of claim 1 further comprising a diaphragm having adhesive on one side for releasably adhering to the rim thereby covering the bell shaped chamber.

17. A head for a stethoscope, for joining to an earpiece assembly comprising:
    a body having a neck portion for joining to the body to the earpiece assembly;
    a bell shaped anterior acoustic chamber and a posterior acoustic chamber in the body, connected by a central passageway, the body having a flat rim surrounding the anterior acoustic chamber;
    a diaphragm having adhesive on one side for releasable adhering to the rim thereby covering the anterior acoustic chamber;
    an acoustic tunnel extending from the posterior acoustic chamber through the neck at substantially a right angle along a straight line to an axis of the anterior chamber for delivering sound waves to the earpiece assembly;
    wherein the posterior chamber has a first reflecting wall portion and a second reflecting portion, the first reflecting wall portion is located on an axis of the anterior shaped acoustic chamber oriented to reflect sound waves to the second wall portion which in turn is oriented to reflect sound waves into the tunnel.

18. The head for a stethoscope of claim 17 wherein an exterior of the body has a plurality of indentations opposite the rim for gripping by a user.

\* \* \* \* \*